United States Patent
Laurenti

(10) Patent No.: US 9,259,258 B2
(45) Date of Patent: Feb. 16, 2016

(54) TORQUE-CONTROLLED SCREWDRIVER FOR MEDICAL USE

(71) Applicant: LAMP S.r.l., Scarmagno (Torino) (IT)

(72) Inventor: Riccardo Laurenti, Scarmagno (IT)

(73) Assignee: LAMP S.R.L., Scarmagno (Torino) (IT)

( * ) Notice: Subject to any disclaimer, the term of this patent is extended or adjusted under 35 U.S.C. 154(b) by 254 days.

(21) Appl. No.: 13/911,198

(22) Filed: Jun. 6, 2013

(65) Prior Publication Data

US 2013/0327190 A1 Dec. 12, 2013

(30) Foreign Application Priority Data

Jun. 6, 2012 (IT) .............................. TO2012A0492

(51) Int. Cl.
*B25B 23/142* (2006.01)
*A61B 17/88* (2006.01)
*A61B 19/00* (2006.01)

(52) U.S. Cl.
CPC ........... *A61B 17/8875* (2013.01); *B25B 23/142* (2013.01); *B25B 23/1427* (2013.01); *A61B 2019/301* (2013.01)

(58) Field of Classification Search
CPC .... B25B 23/14; B25B 23/141; B25B 23/142; B25B 23/1427; A61B 17/8875; A61B 2019/301
USPC .................................................. 81/473–476
See application file for complete search history.

(56) References Cited

U.S. PATENT DOCUMENTS

| | | | |
|---|---|---|---|
| 6,487,943 B1 * | 12/2002 | Jansson et al. ................... | 81/475 |
| 7,762,164 B2 | 7/2010 | Nino et al. | |
| 7,810,416 B2 * | 10/2010 | Cutler et al. .................... | 81/467 |
| 7,938,046 B2 | 5/2011 | Nino et al. | |
| 2008/0016991 A1* | 1/2008 | Gauthier ......................... | 81/474 |
| 2012/0198972 A1* | 8/2012 | Nino et al. ....................... | 81/471 |

FOREIGN PATENT DOCUMENTS

WO 2011/139902 A2 11/2011
WO 2011/139902 A3 11/2011

OTHER PUBLICATIONS

Italian Search Report dated Jan. 8, 2013, for corresponding Italian Patent Application No. TO2012000492 filed on Jun. 6, 2012.

* cited by examiner

*Primary Examiner* — Hadi Shakeri
(74) *Attorney, Agent, or Firm* — Heslin Rothenberg Farley Mesiti, PC; Victor Cardona

(57) ABSTRACT

A torque-controlled screwdriver for medical use includes a hollow maneuvering body, coaxially housed within which are a first bushing and a second bushing provided with respective front toothings for mutual torsional coupling. The first bushing is permanently connected in rotation to the maneuvering body, and the second bushing drives a tool in rotation. The front toothings are configured for disengaging from one another when the screwing torque applied by the maneuvering body to the tool exceeds a predetermined threshold value. A system for enabling a free rotation of a pre-set angular amplitude of the maneuvering body with respect to the tool in the opposite direction to that of screwing is located between the second bushing and the tool.

6 Claims, 4 Drawing Sheets

TORQUE-CONTROLLED SCREWDRIVER FOR MEDICAL USE

CROSS REFERENCE TO RELATED APPLICATIONS

This application claims priority from Italian patent application No. TO2012A000492 filed on Jun. 6, 2012, the entire disclosure of which is incorporated herein by reference.

FIELD OF THE INVENTION

The present invention relates in general to tools for medical use, and more in particular regards a torque-controlled screwdriver designed, for example, to be used for surgical operations.

PRIOR ART

Known from the U.S. Pat. Nos. 7,762,164 and 7,938,046, filed in the name of ECA Medical Instruments is a torque-controlled screwdriver of the above sort, which comprises a hollow manoeuvring body, coaxially housed within which are a first bushing and a second bushing provided with respective front toothings for mutual torsional coupling under the action of an axial-thrust spring. The first bushing is connected in rotation to the manoeuvring body and the second bushing drives in rotation a tool projecting from the manoeuvring body, and the respective front toothings are configured in such a way as to disengage from one another against the action of the thrust spring when the screwing torque applied in use by the manoeuvring body to the tool exceeds a predetermined threshold value. Moreover, this known screwdriver includes a safety system for enabling free rotation of a pre-set angular amplitude of the manoeuvring body with respect to the tool in the opposite direction to that of screwing.

The above safety system has the function of preventing the operator, once the operation of screwing is terminated when the predetermined torque is reached, from possibly erroneously or inadvertently performing a manoeuvre of unscrewing with a consequent reduction of the value of the predetermined tightening torque, with the risks that may derive therefrom from the medical standpoint.

In the case of the aforesaid U.S. Pat. Nos. 7,762,164 and 7,938,046 the safety system is constituted by at least one axial projection radially extending towards the inside of the hollow manoeuvring body and engaged within at least one corresponding external lateral recess of the first bushing, the angular amplitude of which is greater than that of the projection. During the operation of screwing, the rotation imparted on the hollow manoeuvring body is transmitted to the first bushing, and from this to the second bushing and then to the tool, by means of the thrust applied by the projection of the hollow manoeuvring body to the corresponding end wall of the recess of the first bushing. When the hollow manoeuvring body is turned in the direction opposite to that of screwing, the first bushing, and hence the tool, remain uncoupled in rotation from the hollow manoeuvring body while the radial projection of the latter traverses the greater angular amplitude of the recess of the first bushing, as far as the opposite end of said recess.

This solution is not exempt from drawbacks. In particular, even though the greater angular amplitude of the recess of the first bushing should be able to achieve the effect of safety referred to previously, the friction between the radial projection of the hollow manoeuvring body and the bottom wall of said recess may, however, in some cases bring along with it an attendant undesired unscrewing of the first bushing, and hence of the tool of the screwdriver, with a consequent albeit slight unscrewing and unacceptable reduction of the screwing torque applied.

SUMMARY OF THE INVENTION

The object of the invention is to overcome the above drawback and provide a torque-controlled screwdriver of the type referred to above that will prevent the risks referred to previously.

With a view to achieving the above object, the torque-controlled screwdriver according to the invention is basically characterized in that the aforesaid safety means are set between the second bushing and the tool.

More in particular, the safety means include a third bushing carrying the tool and coupled frontally in rotation with the second bushing with an angular play corresponding to the aforesaid pre-set angular amplitude.

In a preferred embodiment, the third bushing has at least one radially extending front projection engaged within a front recess of the second bushing, the amplitude of which is greater than that of the projection, and set between the second and third bushings is a washer with low coefficient of friction.

Thanks to the above arrangement, the torque-controlled screwdriver according to the invention is able to ensure a greater safety against risks of wrong manoeuvres of unscrewing following upon reaching of the pre-set screwing torque.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

Figure 1:
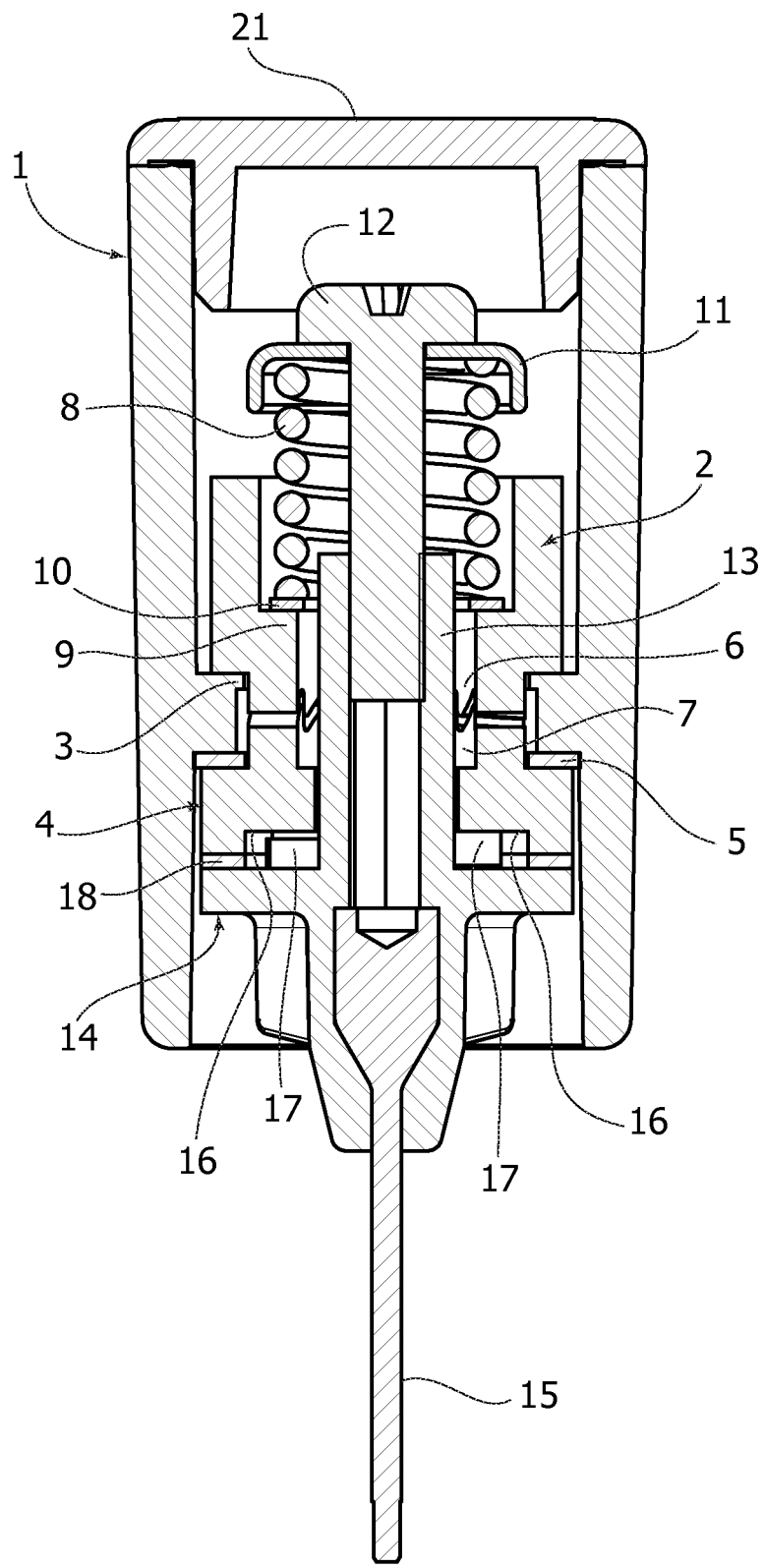
FIG. 1 is a schematic view in axial cross section of a torque-controlled screwdriver according to a preferred embodiment of the invention.

With reference to the drawings, according to a preferred of embodiment of the invention, the torque-controlled screwdriver comprises a hollow manoeuvring body 1, coaxially housed within which are a first annular bushing 2, set resting against the upper side of an internal annular flange 3 of the body 1, and a second annular bushing 4 set resting against the underside of the flange 3, with the interposition of a washer 5 made of a material with low coefficient of friction, for example, Teflon.

The first bushing 2 and the second bushing 4 are formed with respective front toothings 6, 7 normally meshing with one another under the action of an axial-thrust spring 8.

The spring 8 reacts, at the bottom, against an internal shoulder 9 of the first bushing 2, with the interposition of a washer 10 and, at the top, against a cup 11 carried by a screw 12 which screws within a tubular appendage 13 of a third bushing 14, the appendage 13 extending axially through the bushings 2 and 4.

The third bushing 14 is set underneath the second bushing 4 and carries a tool 15, in particular the tip of a screwdriver, projecting on the outside of the hollow manoeuvring body 1.

Figure 4:
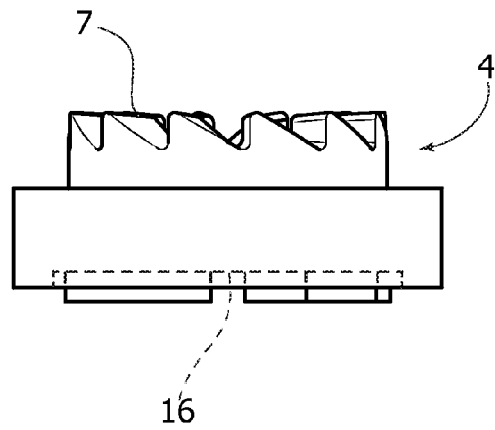
FIG. 4 is a side elevation at a larger scale of one component of the screwdriver.
Figure 5:
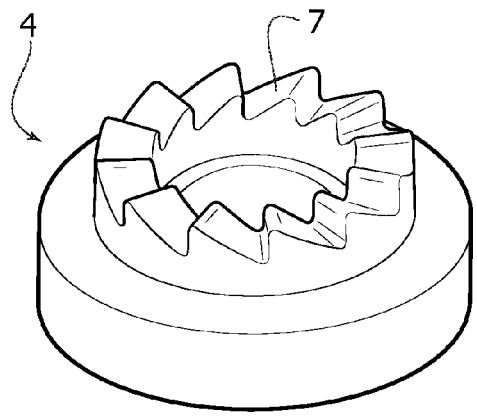
FIGS. 5 and 6 are two perspective views from above and beneath, respectively, of the component of FIG. 4.
Figure 6:
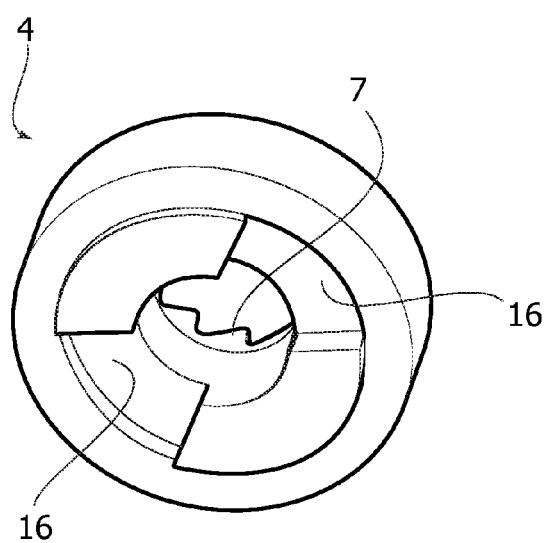

As is illustrated in detail in FIGS. 4 to 6, the second bushing 4 is formed, on the side opposite to the toothing 7, i.e., on its surface facing the third bushing 14, with a pair of front recesses 16, inserted within which are respective radially extending front projections 17 of the third bushing 14. The angular amplitude of the recesses 16 is considerably greater than the width of the front projections 17 so as to define a pre-set degree of free rotation of the second bushing 4 with respect to the third bushing 14, which will be described in what follows.

Set between the second bushing 4 and the third bushing 14 is a washer 18 made of a material with low coefficient of friction, for example, Teflon.

Figure 2:
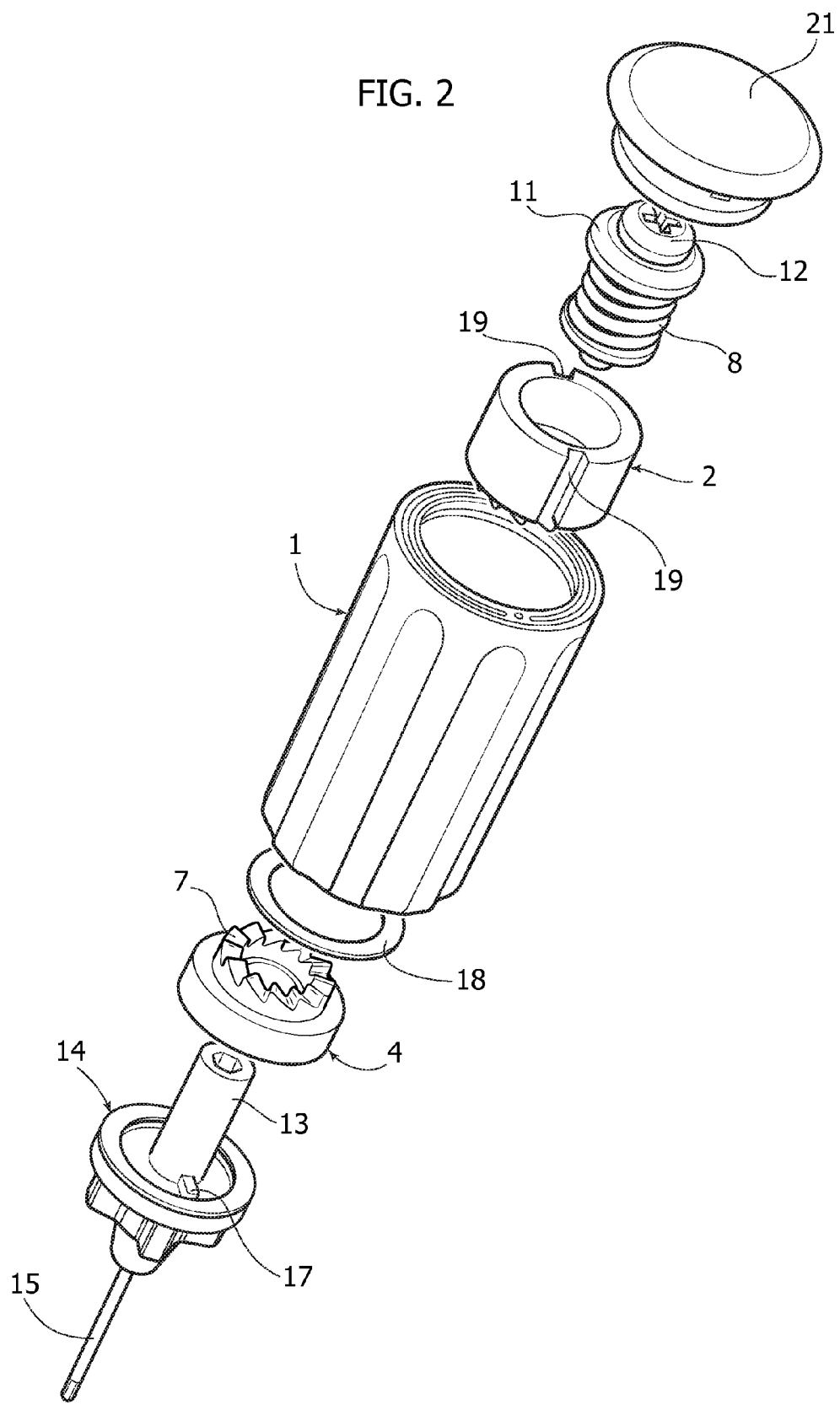
FIG. 2 is an exploded perspective view of the screwdriver.
Figure 3:
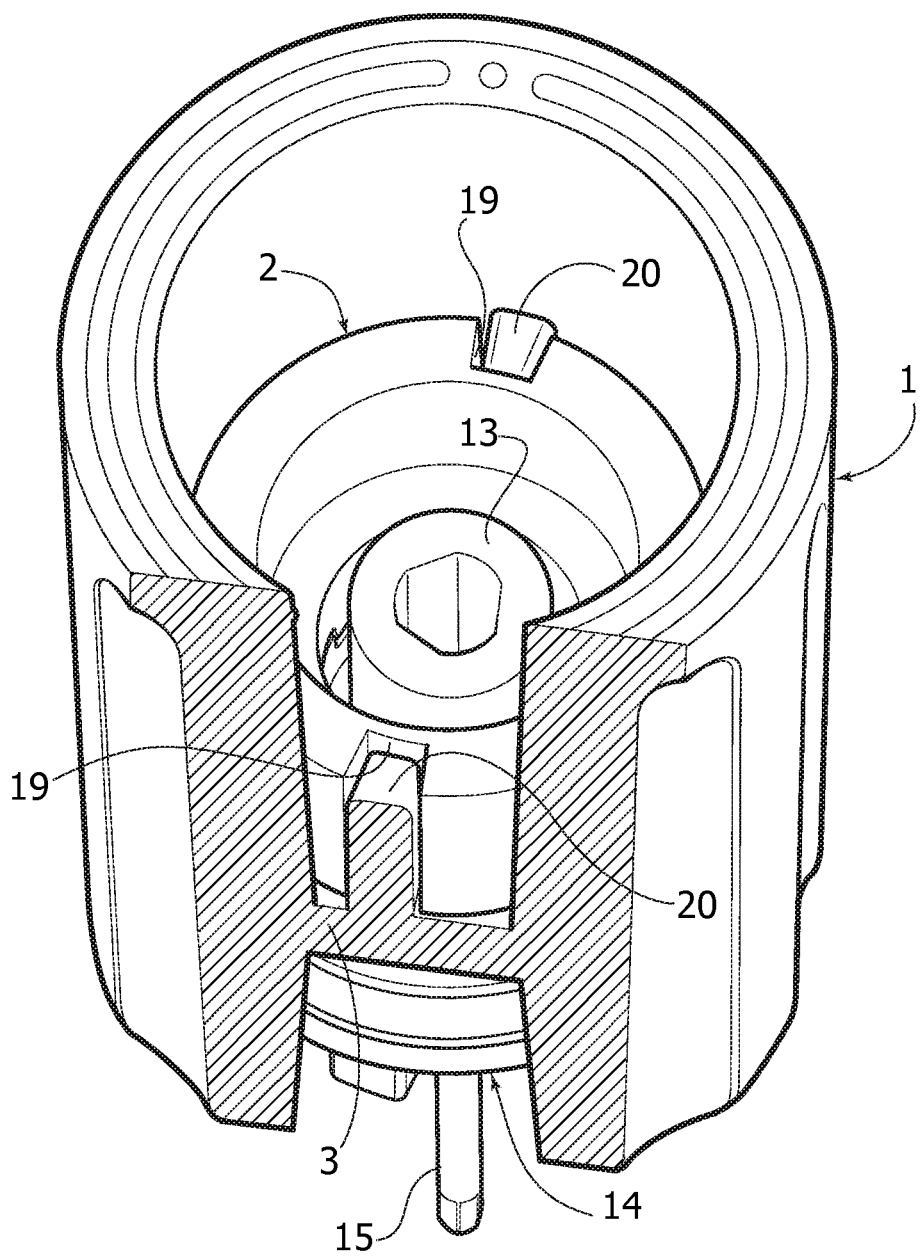
FIG. 3 is a partially sectioned perspective view at a larger scale of a part of the screwdriver.

With reference in greater detail to FIGS. 2 and 3, the first bushing 2 is formed with a pair of axial grooves 19 set opposite to one another, engaging within which, substantially without angular play, are respective internal radial projections 20 of the hollow manoeuvring body 1. Consequently, the first bushing 2 is permanently coupled in rotation to the manoeuvring body 1.

The screwdriver is completed by a plug 21 applied to the end of the hollow manoeuvring body 1 opposite to the tool 15.

With the arrangement described above, operation of the torque-controlled screwdriver according to the invention is described in what follows.

When the hollow manoeuvring body 1 is turned in the screwing direction, normally clockwise, the rotation is transmitted to the first bushing 2, then to the second bushing 4 through the toothings 6 and 7, and finally to the third bushing 14 and to the tool 15 via the thrust applied by the projections 17 against corresponding ends of the recesses 16.

When a pre-set value of torque is reached during the screwing step, the calibration of the spring 8 is such that it enables the teeth 6 of the first bushing 2 to climb on the teeth 7 of the second bushing 4, causing mutual disengagement thereof. Consequently, in this condition, a further rotation of the manoeuvring body 1 in the screwing direction is not transmitted to the tool 15. Nor is a possible rotation transmitted in the opposite direction, i.e., in the direction of unscrewing, throughout the angular range corresponding to the amplitude of the recesses 16, i.e., until the opposite ends of said recesses 16 set themselves again in contact with the projections 17 of the third bushing 14. In this step, the rotation of the second bushing 4 with respect to the third bushing 14, kept stationary, is obtained with the minimum friction between the two bushings thanks to the presence of the washer 18, which prevents the risk of the third bushing 14 in some way possibly being involuntarily drawn along in rotation by friction. In this way, the safety of the screwdriver according to the invention as regards possible manoeuvring errors, when the pre-set screwing torque is reached, is appreciably improved.

The screwdriver according to the invention may be manufactured in a relatively inexpensive way and is conveniently disposable.

Of course, the details of construction and the embodiments may vary widely with respect to what has been described and illustrated herein, without thereby departing from the scope of the present invention as defined in the ensuing claims.

What is claimed is:

1. A torque-controlled screwdriver for medical use, comprising:
    a hollow manoeuvring body, coaxially housed within which are a first bushing and a second bushing provided with respective front toothings for mutual torsional coupling under the action of an axial-thrust spring;
    the first bushing being connected in rotation to the manoeuvring body and the second bushing driving in rotation a tool projecting from the manoeuvring body;
    said front toothings being configured so as to disengage from one another, against the action of said thrust spring, when the screwing torque applied by the manoeuvring body to the tool exceeds a predetermined threshold value; and
    safety means for enabling a free rotation of a pre-set angular amplitude of the manoeuvring body with respect to the tool in the opposite direction to that of screwing, wherein said safety means are arranged between the second bushing and the tool,
    wherein said safety means include a third bushing carrying the tool and coupled frontally in rotation with the second bushing with angular play corresponding to said pre-set angular amplitude.

2. The screwdriver according to claim 1, wherein the third bushing has at least one radially extending front projection engaged within a front recess of the second bushing, the amplitude of which is greater than that of said projection.

3. The screwdriver according to claim 1, wherein set between said second and third bushings is a washer made of a material with low coefficient of friction.

4. The screwdriver according to claim 1, wherein said manoeuvring body has an internal annular flange against which said second bushing rests frontally, on the side opposite to said third bushing, with the interposition of a washer made of a material with low coefficient of friction.

5. The screwdriver according to claim 1, wherein said third bushing has a tubular shank that traverses axially said second and first bushings and engaged in which is a screw bearing a resting member for one end of said thrust spring, an opposite end of said spring reacting against said first bushing.

6. The screwdriver according to claim 1, wherein said first bushing is permanently coupled in rotation to the manoeuvring body.

* * * * *